US00RE41448E

(19) United States
(12) Reissued Patent
Squitieri

(10) Patent Number: US RE41,448 E
(45) **Date of Reissued Patent: *Jul. 20, 2010**

(54) SQUITIERI HEMODIALYSIS AND VASCULAR ACCESS SYSTEMS

(75) Inventor: Rafael P. Squitieri, Wilton, CT (US)

(73) Assignee: Hemosphere, Inc., Eden Prairie, MN (US)

( * ) Notice: This patent is subject to a terminal disclaimer.

(21) Appl. No.: 10/219,998

(22) Filed: Aug. 15, 2002

Related U.S. Patent Documents

Reissue of:
(64) Patent No.: 6,102,884
Issued: Aug. 15, 2000
Appl. No.: 08/835,316
Filed: Apr. 7, 1997

U.S. Applications:
(60) Provisional application No. 60/037,094, filed on Feb. 3, 1997.

(51) Int. Cl.
*A61M 37/00* (2006.01)

(52) U.S. Cl. ..... 604/8; 604/4.01; 604/5.01; 604/6.01

(58) Field of Classification Search ..... 604/4.01, 604/5.01, 6.168, 523, 175, 27, 264–266, 604/533, 288.01–288.03, 284, 508; 623/1.1, 623/1.36, 1.43, 1.49, 11.1, 902–903
See application file for complete search history.

(56) References Cited

U.S. PATENT DOCUMENTS 3,683,926 A * 8/1972 Suzuki ..... 606/154
3,818,511 A 6/1974 Goldberg et al.
3,882,862 A 5/1975 Berend
4,318,401 A * 3/1982 Zimmerman ..... 604/28
4,447,237 A 5/1984 Frisch et al.
4,496,349 A 1/1985 Cosentino
4,619,641 A 10/1986 Schanzer
4,822,341 A * 4/1989 Colone ..... 604/175
4,877,661 A 10/1989 House et al.
4,898,669 A * 2/1990 Tesio ..... 210/232

(Continued)

FOREIGN PATENT DOCUMENTS

DE 4418910 * 7/1995

(Continued)

OTHER PUBLICATIONS

Alan S. Coulson, M.D., Jagjit Singh, M.D., Joseph C. Moya, "Modification of Venous End of Dialysis Grafts: An Attempt to Reduce Neointimal Hyperplasia," *Dialysis& Transplantation*, vol. 29, No. 1, Jan. 2000, pp. 10 to 18.

(Continued)

*Primary Examiner*—Leslie R Deak
(74) *Attorney, Agent, or Firm*—Knobbe, Martens, Olson & Bear, LLP

(57) ABSTRACT

A hemodialysis and vascular access system comprises a subcutaneous composite PTFE silastic arteriovenous fistula having an indwelling silastic venous end which is inserted percutaneously into a vein and a PTFE arterial end which is anastomosed to an artery. Access to a blood stream within the system is gained by direct puncture of needle(s) into a needle receiving site having a tubular passage within a metal or plastic frame and a silicone upper surface through which needle(s) are inserted. In an alternate embodiment of the invention, percutaneous access to a blood stream may be gained by placing needles directly into the system (i.e. into the PTFE arterial end). The invention also proposes an additional embodiment having an arterialized indwelling venous catheter where blood flows from an artery through a tube and a port into an arterial reservoir and is returned to a vein via a port and a venous outlet tube distinct and distant from the area where the blood from the artery enters the arterial reservoir. The site where blood is returned to the vein is not directly fixed to the venous wall but is free floating within the vein. This system provides a hemodialysis and venous access graft which has superior longevity and performance, is easier to implant and is much more user friendly.

46 Claims, 8 Drawing Sheets

U.S. PATENT DOCUMENTS

| | | | | | |
|---|---|---|---|---|---|
| 4,929,236 | A | * | 5/1990 | Sampson | 604/175 |
| 4,955,899 | A | | 9/1990 | Della Corna et al. | |
| 5,041,098 | A | | 8/1991 | Loiterman et al. | |
| 5,192,310 | A | * | 3/1993 | Herweck et al. | 623/1.27 |
| 5,197,976 | A | * | 3/1993 | Herweck et al. | 623/1.27 |
| 5,399,168 | A | * | 3/1995 | Wadsworth et al. | 604/175 |
| 5,476,451 | A | * | 12/1995 | Ensminger et al. | 604/288.03 |
| 5,558,641 | A | * | 9/1996 | Glantz et al. | 604/288.02 |
| 5,562,618 | A | * | 10/1996 | Cai et al. | 604/288.02 |
| 5,591,226 | A | | 1/1997 | Trerotola et al. | |
| 5,607,463 | A | | 3/1997 | Schwartz et al. | |
| 5,637,088 | A | * | 6/1997 | Wenner et al. | 604/93.01 |
| 5,637,102 | A | * | 6/1997 | Tolkoff et al. | 604/536 |
| 5,676,346 | A | * | 10/1997 | Leinsing | 251/149.1 |
| 5,743,894 | A | * | 4/1998 | Swisher | 604/320 |
| 5,755,775 | A | * | 5/1998 | Trerotola et al. | 606/194 |
| 5,792,104 | A | * | 8/1998 | Speckman et al. | 604/288.02 |
| 5,797,879 | A | * | 8/1998 | DeCampli | 604/93.01 |
| 5,800,512 | A | | 9/1998 | Lentz et al. | |
| 5,830,224 | A | * | 11/1998 | Cohn et al. | 606/167 |
| 5,840,240 | A | | 11/1998 | Stenoien et al. | |
| 5,866,217 | A | | 2/1999 | Stenoien et al. | |
| 5,904,967 | A | * | 5/1999 | Ezaki et al. | 428/36.92 |
| 5,931,865 | A | | 8/1999 | Silverman et al. | |
| 6,001,125 | A | | 12/1999 | Golds et al. | |
| 6,019,788 | A | * | 2/2000 | Butters et al. | 623/1.35 |
| 6,036,724 | A | | 3/2000 | Lentz et al. | |
| 6,102,884 | A | | 8/2000 | Squitieri | |
| 6,156,016 | A | | 12/2000 | Maginot | |
| 6,261,255 | B1 | | 7/2001 | Mullis et al. | |
| 6,338,724 | B1 | * | 1/2002 | Dossa | 604/8 |
| 6,398,764 | B1 | * | 6/2002 | Finch et al. | 604/284 |
| 6,402,767 | B1 | | 6/2002 | Nash et al. | |
| 6,428,571 | B1 | | 8/2002 | Lentz et al. | |
| 6,582,409 | B1 | * | 6/2003 | Squitieri | 604/288.01 |
| 6,719,783 | B2 | | 4/2004 | Lentz et al. | |
| 2002/0049403 | A1 | | 4/2002 | Alanis | |
| 2003/0004559 | A1 | | 1/2003 | Lentz et al. | |
| 2004/0193242 | A1 | | 9/2004 | Lentz et al. | |
| 2004/0215337 | A1 | | 10/2004 | Hain et al. | |
| 2005/0137614 | A1 | | 6/2005 | Porter et al. | |
| 2005/0203457 | A1 | | 9/2005 | Smego | |
| 2005/0215938 | A1 | | 9/2005 | Khan et al. | |
| 2006/0064159 | A1 | | 3/2006 | Porter et al. | |
| 2007/0123811 | A1 | | 5/2007 | Squiteri | |
| 2007/0167901 | A1 | | 7/2007 | Herrig et al. | |

FOREIGN PATENT DOCUMENTS

| | | |
|---|---|---|
| DE | 44 18 910 A1 | 12/1995 |
| DE | 295 15 546 U1 | 3/1997 |
| JP | 57-14358 | 1/1982 |
| JP | 58-168333 | 11/1983 |
| JP | 04-507050 | 12/1992 |
| JP | 05-212107 | 8/1993 |
| JP | 06-105798 | 4/1994 |
| JP | 09-84871 | 3/1997 |
| WO | WO 84/03036 | 8/1984 |
| WO | WO 95/19200 | 7/1995 |
| WO | WO 96/24399 | 8/1996 |

OTHER PUBLICATIONS

A.S. Coulson, M.D., Ph.D, Judy Quarnstrom, I.V.N., J. Moshimia, M.D., "A Combination of the Elephant Trunk Anastomosis Techinique and Vascular Clips for Dialysis Grafts," *Surgical Rounds*, Nov. 1999, pp. 596 to 608.

International Search Report for PCT Application No. PCT/US98/01939 dated May 5, 1998 in 3 pages.

Search Report for EP Application No. 05006233.0 dated Jun. 8, 2005 in 2 pages.

The Office Action dated Dec. 17, 2008 issued in Co–Pending Appl. No. 11/417,658 in 11 pages.

The Amendment dated Mar. 17, 2009 filed in Co–Pending Appl. No. 11/417,658 in 2 pages.

Interview Summary dated Mar. 11, 2009 for Co–Pending Appl. No. 11/417,658 in 4 pages.

* cited by examiner

Amended
FIG. 5
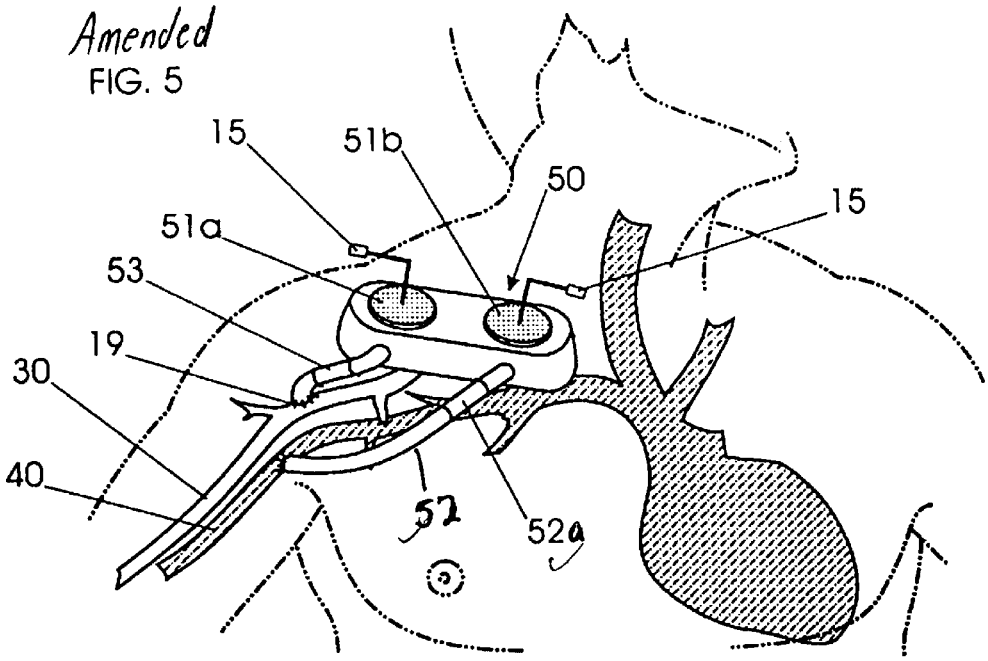
Amended
FIG. 6
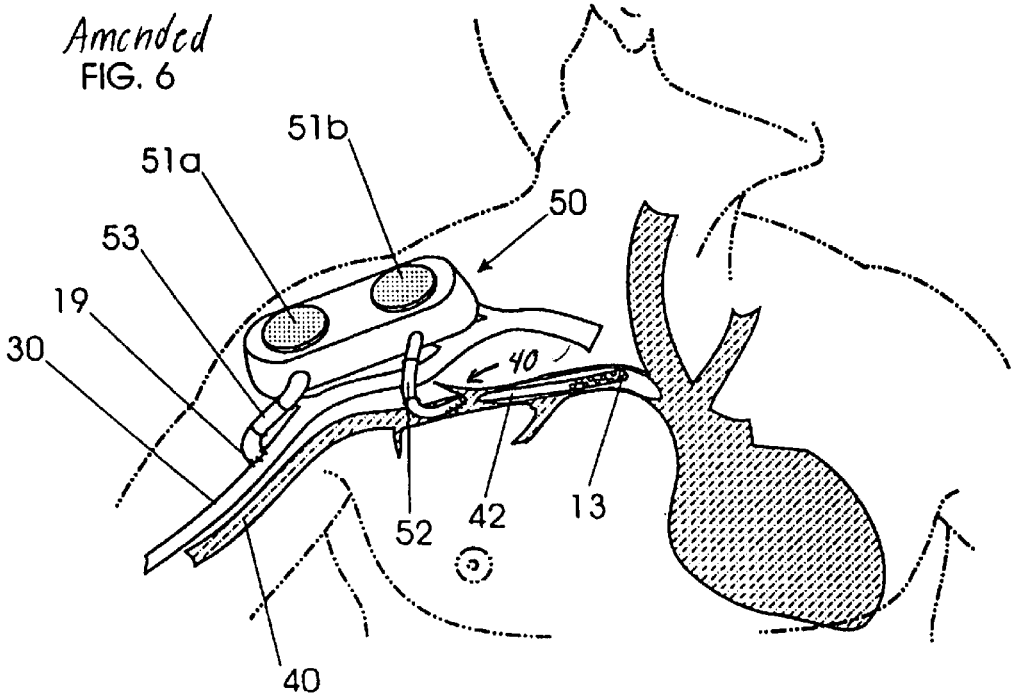

Amended
FIG. 7
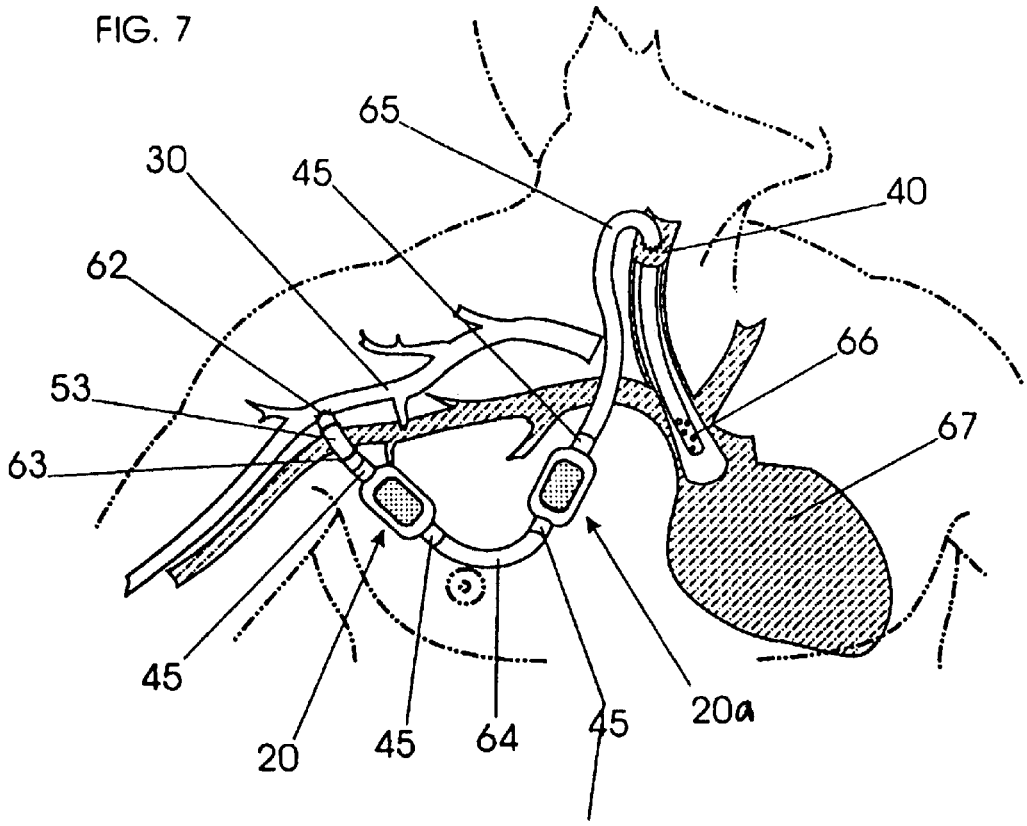

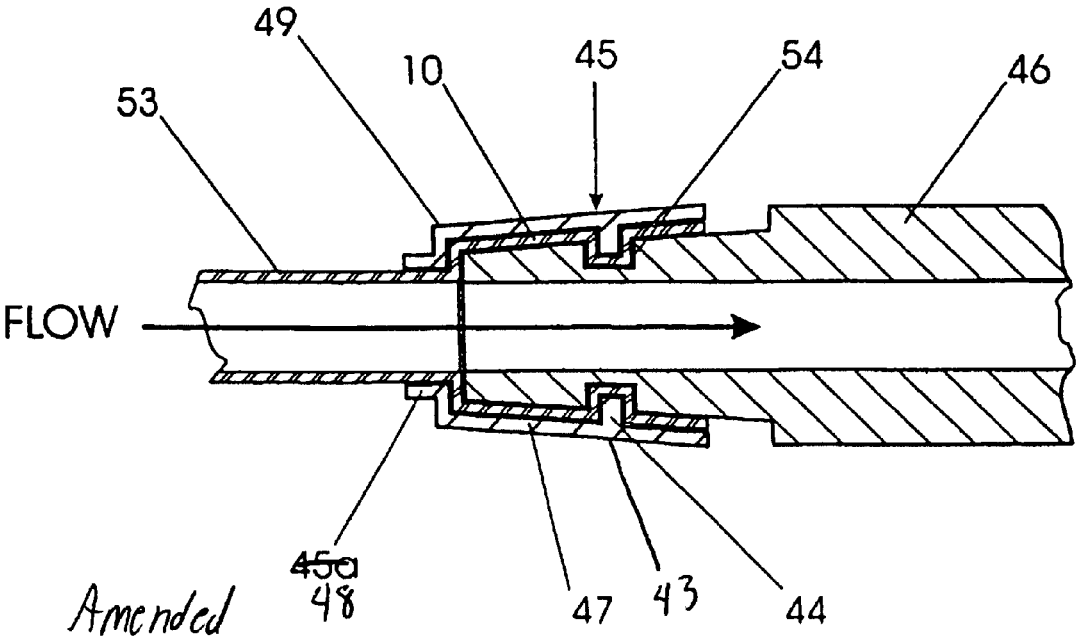
Amended
FIG.11

Amended
FIG. 14
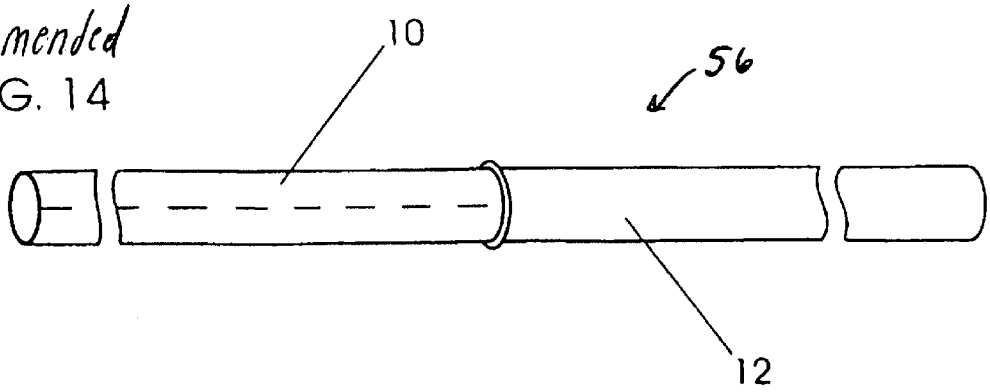

SQUITIERI HEMODIALYSIS AND VASCULAR ACCESS SYSTEMS

Matter enclosed in heavy brackets [ ] appears in the original patent but forms no part of this reissue specification; matter printed in italics indicates the additions made by reissue.

*This is a reissue application of U.S. Pat. No. 6,102,884, which issued on Aug. 15, 2000, and which claims benefit under 35 U.S.C. Section 119(e) to U.S. Provisional Patent Application Ser. No. 60/037,094, filed Feb. 3, 1997.*

*Notice: More than one reissue application has been filed for the reissue of U.S. Pat. No. 6,102,884. The reissue applications are U.S. application Ser. No. 10/219,998 (the present application) and U.S. application Ser. No. 11/417,658, which is a continuation reissue of U.S. Pat. No. 6,102,884.*

BACKGROUND OF THE INVENTION

Currently, HD (hemodialysis) and vascular access for chemotherapy and plasmapheresis is achieved in one of several ways. Applicant's invention involves a new method and instrumentation for HD and vascular access designed to eliminate the problems of the prior methods and create a new, more durable, easier to use, vascular access system.

One prior art method involves a primary arteriovenous fistula. In this method, a native artery is sewn to a native vein creating a high flow system of blood in a vein which over time can be accessed with two hemodialysis needles attached to a dialysis machine. The problem with this method is that few patients are candidates secondary to anatomy and in others the veins or shunt fail to enlarge and mature properly even if the primary fistula remains patent. These arteriovenous fistulas also become aneursymbol over time requiring revision.

Another method involves a subcutaneous prosthetic conduit (PTFE) in the shape of a tube which is sewn at either end to openings made in an artery and vein. This method causes recurrent stenosis at the venous outflow leading to thrombosis (i.e., graft closure) secondary to intimal hyperplasia at venous anastomosis. Thrombosis also occurs at needle puncture sites along the PTFE.

Another method involves a "tunneled" percutaneous dual lumen catheter which is inserted into a central vein. This causes recurrent thrombosis secondary to stasis of blood in the lumen (i.e., not a continuous flow system like an A-V fistula) and build up of fibrinous debris at the venous end. Further, the access end of the catheter protrudes through the skin making it cosmetically unappealing, cumbersome to live with, as well as more likely to become infected.

A further method involves the use of the Sorenson Catheter. This is a percutaneous (not tunneled) dual lumen catheter, placed into the central venous system, which is used to provide temporary access for the purposes of hemodialysis. These catheters are prone to kinking, clotting, infection, and poor flow rates.

A still further method of vascular access involves the "Porta-a-cath". This system of venous access, which utilizes a subcutaneous reservoir attached to a central venous catheter, is used for long term intervenous access for chemotherapy etc. (It is not intended for HD.) The ports are prone to clotting and must be continually flushed since they are a stagnant system.

Applicant's invention involves a vascular access system, known as the Squitieri Hemodialysis and Vascular Access System, which creates a continuous blood flow and which is easily accessed and resistant to clotting. These advantages provide ideal access for long term HD, chemo or blood draws. An example, would be patients who are on coumadin which require weekly blood draws. This new system becomes less painful over time as the skin over the "needle access" site become less sensitive. The veins are spared repeated blood draws which results in vein thrombosis to such a degree that some patients "have no veins left" making routine blood draws impossible.

Among the more relevant prior art patents are U.S. Pat. Nos. 4,898,669; 4,822,341; 5,041,098; and, 4,790,826. None of the foregoing patents disclose a system having the features of this inventions

SUMMARY OF THE INVENTION

A hemodialysis and vascular access system comprises a PTFE end which is sutured to an opening in an artery at one end and the other end is placed into a vein using any technique which avoids the need for an anastomosis between the silicone "venous" end of the catheter and the vein wall. The system comprises any material, synthetic or natural (i.e. vein) which can be sutured to the artery (i.e. preferably PTFE) at one end while the other end is composed of a material which is suitable for placement into a vein in such a way that the openings in the "venous" end of the system are away from the site where the graft enters the vein. The system may also be constructed of multiple layers of materials i.e. PTFE on the inside with silastic on the outside. The "Needle Receiving Site" may also be covered with PTFE to encourage self sealing and tissue ingrowth.

A preferred embodiment comprises a combination of PTFE conduit sewn to an artery on one end of the system with the other end connected to a silastic-plastic catheter which can be percutaneously inserted into a vein via an introducer. The venous end may also be placed via open cut down. The seal around the system where it enters the vein may be "self sealing" when placed in percutaneous technique; it may be achieved with a purse string when done by open technique "cut down"; or, it may be sewn to the vein to create a seal with a "cuff" while the system continues downstream within the venous system to return the arterial blood away from the site of entry into the vein. The entire system can be positioned subcutaneously at the completion of insertion. This design is a significant improvement over existing methods because it avoids the most frequent complication of current HD access methods. By utilizing an indwelling venous end, one avoids creating a sewn anastomosis on a vein which is prone to stenosis secondary to neointimal hyperplasia. By having continuous flow through the silastic end of the catheter, thrombosis of these catheters can be avoided. Dialysis is made more efficient by decreasing recirculation of blood which accompanies the use of side by side dual lumen catheters inserted into a central vein. This invention not only benefits the patient but it also speeds dialysis thus saving time and money.

To summarize, the Squitieri Access System comprises a tube composed of PTFE and a silastic catheter. This tube is used to create an arteriovenous fistulu. The PTFE end (arterial end) of the tube is sewn to an artery while the silastic catheter end is placed into the venous system by the Seldinger technique much like a standard central line. The entire system is subcutaneous at the completion of insertion. This system is a composite of the arterial end of a "gortex graft" joined to the venous end of a "permacath". This system enjoys strengths of each type of access and at the same time avoids their weaknesses.

Accordingly, an object of this invention is to provide a new and improved vascular access system.

Another object of this invention is to provide a new and improved hemodialysis and vascular access system including an easily replaceable needle receiving site which has superior longevity and performance, is more easily implanted, more easily replaced, and is "user friendly" i.e. easily and safely accessed by a nurse or patient which is ideal for home hemodialysis.

A more specific object of this invention is to provide a new and improved Squitieri hemodialysis and vascular access system including a subcutaneous composite PTFE/Silastic arteriovenous fistula.

A further object of this invention is to provide a new and improved hemodialysis and vascular access system including a fistula utilizing an indwelling silastic end which is inserted percutaneously into the venous system and a PTFE arterial end which is anastomosed to an artery and including a unique needle receiving sites which are positioned anywhere between the ends and which have superior longevity and performance.

A further object of this invention is to provide a system constructed to preserve laminar flow within the system and at the venous outflow end to reduce turbulence and shear force in the vascular system to the degree possible.

A still further object of this invention is to provide a system wherein the arterial end (PTFE) may also be placed by percutaneous technique including one where blood entry holes are distant from the site where blood enters the veins.

BRIEF DESCRIPTION OF THE DRAWINGS

The above and other objects of this invention may be more clearly seen when viewed in conjunction with the accompanying drawings wherein:

FIG. 5 is a perspective view of an alternate embodiment of the invention with one port having a tube sewn to a vein;

FIG. 6 is a perspective view of the embodiment in FIG. 5 with a silastic tube floated down a vein;

FIG. 7 illustrates a ringed tube sewn to an artery and connected to a first access site which is joined to a second site by silastic tubing and includes an outflow through silastic tubing which is floated into the venous system;

FIG. 11 discloses a quick coupler design utilized in conjunction with the system;

FIG. 13 shows holes where ports can be fixed in place while

DETAILED DESCRIPTION OF THE INVENTION

Figure 1:
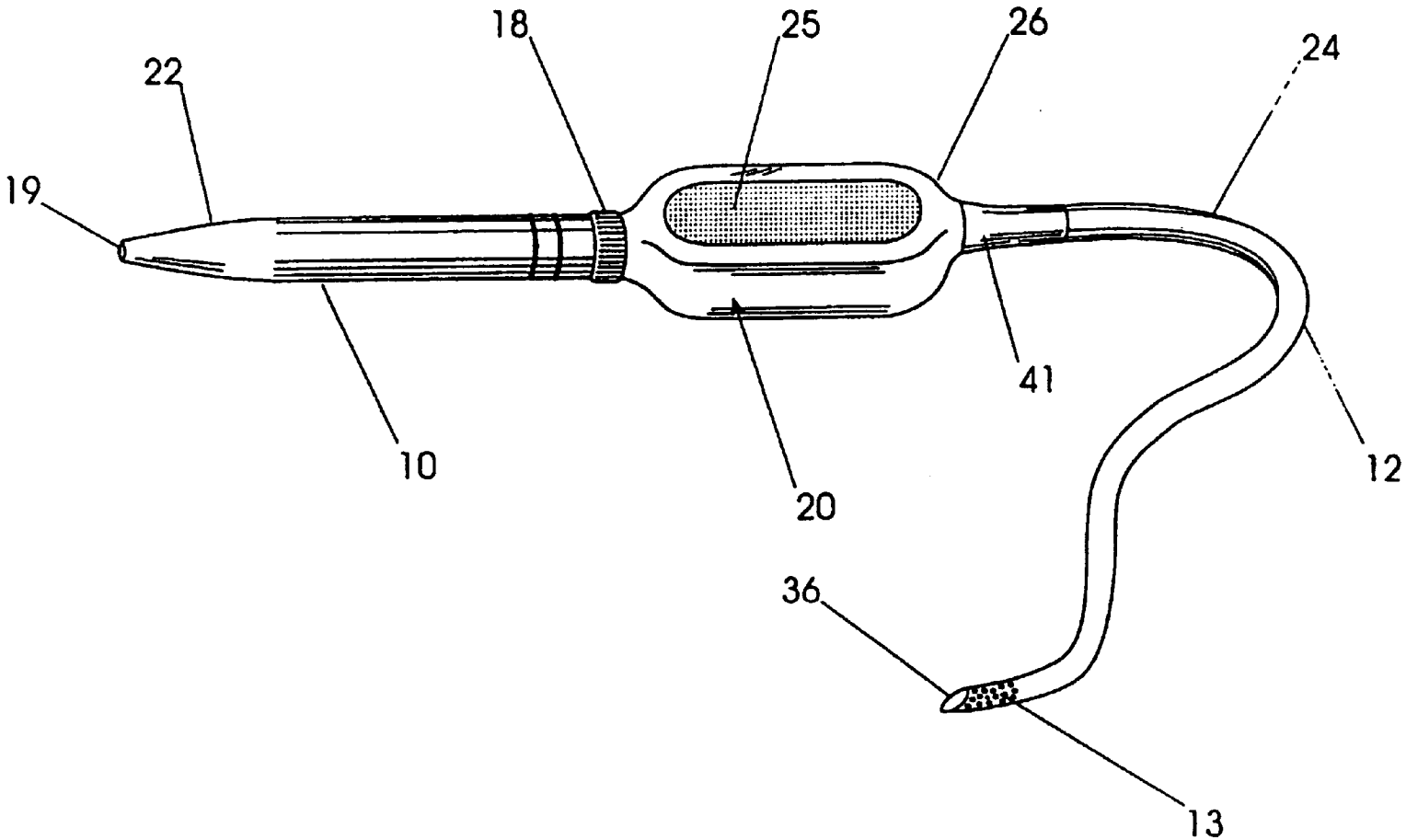
FIG. 1 is a perspective view of the vascular access system comprising the invention.

Referring to the drawings the Squitieri hemodialysis and vascular system, as shown in FIG. 1, comprises a PTFE/dacron (or other synthetic or natural material) tube 10 of several centimeters in length which is attached at one end by means of a coupling 11 to a needle access site 20. Adjustable band 18 regulates the blood flow through the access site 20. The PTFE tube 10 is approximately 7 mm in diameter and transitions downward to an open end portion 19 approximately 4 mm in diameter.

Figure 2:
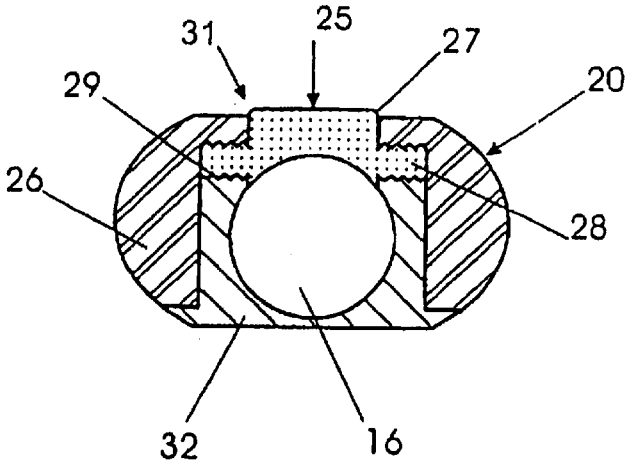
FIG. 2 is a cross-sectional view of the needle access site taken along the line 2—2 of FIG. 1.

The access site 20 includes an in line aperture 16, see FIG. 2, having a silicone tube 41 connected thereto at one end leading to a long flexible plastic/silastic/silicone tube 12 with transverse holes 13 along its free end. The number of holes 13 may vary within predetermined limits to achieve optimum results. The end 36 may be beveled for ease of insertion. This tubular arrangement functions as a subcutaneous connection between the arterial and venous systems. It may also be modified to allow part of the system to exit through the skin 14 to provide access to the blood circulation without placing needles 15 through the skin 14 into the fistula (usually at the PTFE end).

Along the length of the catheter specially constructed access segments 20 are located to receive specially designed needles 15 into the system to gain access to the blood stream which flows through aperture 16. This method avoids perigraft bleeding which leads to thrombosis either by compression of the graft by hematoma or by manual pressure applied to the graft in an attempt to control the bleeding.

The needle access areas 20 which are designed to receive needles 15 etc. to allow access to the system are in line conduits with self-sealing material 17 such as silicone located beneath the skin surface. The silicone member 25 comprises an oval configuration exposed within the frame 26 for ease of puncture. The system may be accessed immediately after insertion without having to wait for the graft to incorporate into the tissues as is the case with the current methods of subcutaneous fistulas. These access areas 20 will protect the graft since they are uniformly and easily utilized requiring little training or experience. The "needle receiving" sites 20 are designed in such a way to preserve laminar flow as far as possible (i.e. not a reservoir arrangement). Needle receiver sites 20 may be connected to a system via "quick couple" 45 for easy exchangability, see FIG. 11.

Figure 3:
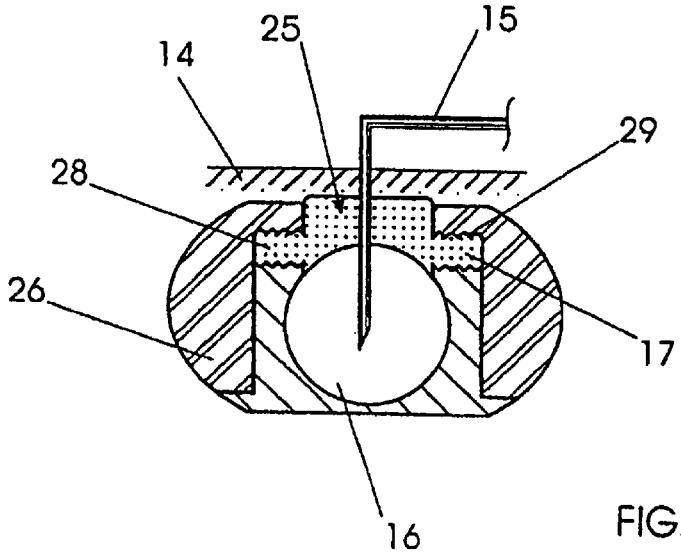
FIG. 3 is a cross-sectional view similar to FIG. 2 with a needle inserted into the access site.

FIGS. 2 and 3 disclose a needle access site 20 wherein a silicone member 25 is mounted within a plastic or metal frame 26. A protruding portion 27 of member 25 extends upwardly through the aperture 31 while a flange portion 28 extends outwardly on both sides of the portion 27 to be gripped by teeth 29 on the internal surface of frame 26 and member 32. The member 26 includes a passage 16 for blood flow. The blood flow is accessed by inserting needles 15 through the silicone 25 which is preferably oval in shape. The teeth 29 seal the arterial pressure. The internal chamber 16 of the needle receiving site 20 is tubular in shape.

The free end 19 of the PTFE tube 10 is sewn to an opening in an artery 30, see FIG. 7, while the plastic end 24 having been inserted percutaneously lies in the venous system in such a way that the openings 13 in the silastic tube 12 are downstream from the site where the flexible plastic tube 24 enters the vein 40. The venous end may be inserted via "cut-down". The purpose of the system is to allow communication between an artery 30 and a vein 40 in such a way that the system may be accessed by either puncturing the PTFE segment or by entering the specialized "needle receiving" site 20. This allows blood to flow from the system to a hemodialysis machine (not shown) and then return into the venous outflow portion at a more distal (venous end) location allowing the blood 35 to return from the HD machine (not shown) back into the patient.

Figure 4:
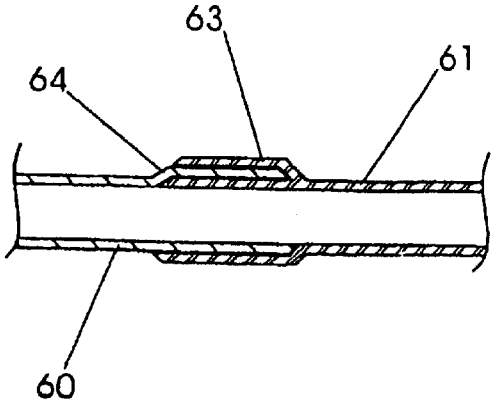
FIG. 4 is a cross-sectional view of the coupling between the PTFE and the silicone venous end of the catheter.

FIG. 4 discloses, as an alternative, a "glued" connection between PTFE tubing 60 and silicone tubing 61 wherein the PTFE 61 is inserted into an enlarged portion of silicone 61 wherein the longitudinally extending portion includes a raised section 63 which locks a raised section 64 of PTFE 61 within the silicone 60.

In this invention, the materials used may vary as specified herein. The system may be constructed of one or more specific materials. The arteries and veins used may also vary. Material may also be covered with thrombus resistant coatings (heparin, etc.) or biologic tissue. The system may in specific cases be "ringed" for support.

The same concept of using an arterialized venous access catheter may be applied to the use of long term indwelling catheters used to give chemotherapy etc., making the current ports obsolete as these new access systems will have a decreased thrombosis and they will no longer need to be flushed as continuous blood flow through the system makes thrombus formation unlikely. This will definitely cut down on costs since it will decrease nursing requirements in out patient settings, etc.

In alternate embodiments shown in FIGS. 5 and 6, the system comprises an arterial reservoir structure or port 50 with a needle accessible top portion [51] preferably constructed of silicone. The reservoir 50 is connected to an outlet tube 53 of PTFE (gortex-ringed), which is sewn to an artery 30 at its other end. The venous outlet tube 52 is constructed in a similar way but it is either sewn to a vein 40 via gortex ringed portion [52] *52a* or is placed percutaneously into the central circulation via an indwelling venous (silicon) catheter 42 as shown in FIG. 6. There is no continuous flow through this version of the system since the ports are not connected. Flow is established when the system is attached to an HD machine with a needle 15 in the arterial port 51a to deliver blood to the HD machine and a second needle 15 is placed in the venous port 51b to the vein 40 to deliver blood to the patient. The ports 51a, 51b will remain flushed with heparin when not in use to avoid clotting when accessed through the skin 14 with needles 15. The ports 51a, 51b will also provide high flow access to both the arterial and venous systems. FIG. 6 shows two separate ports 51a and 51b with [one] *the* tube 53 sewn to an artery 30 and the other tube 42 floated down a vein 40.

FIG. 7 illustrates in an anatomical drawing, a ringed gortex tubing 53 sewn to an artery 30 at 62 and coupled at its other end 63 to the needle access site 20. The site 20, see FIGS. 1–3, is joined by silastic tubing 64 to a second access site 20a which has an outlet silastic tube 65. The outlet tube 65 includes a plurality of perforations 66 at its outlet end which is positioned in the venous system 67 through vein 40. Either site 20 or 20a can be used for needle access.

Figure 8:
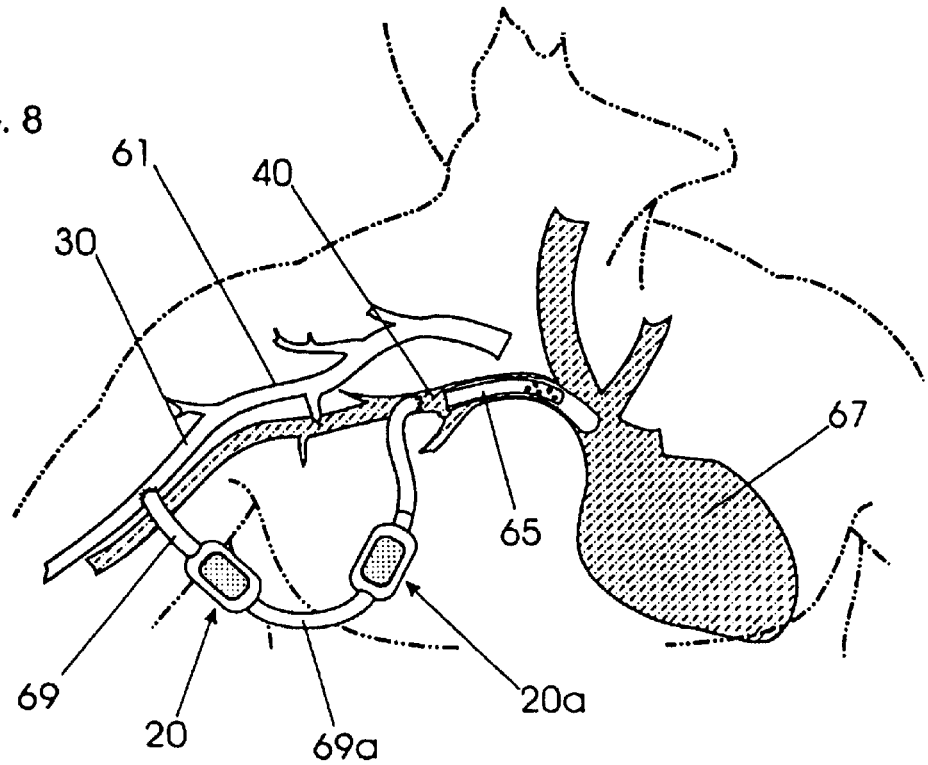
FIG. 8 is similar to FIG. 7 but shows PTFE sewn to an artery and silastic tubing floated into a different portion of the venous system.

FIG. 8 depicts an embodiment similar to that of FIG. 7 except that the coupling between the artery 30 and the first needle access site 20 is PTFE tube 69. The entry to the venous system 67 is via vein 40 which has silastic tubing 65 floated therein. 69a depicts PTFE joining parts 20 and 20a.

Figure 9:
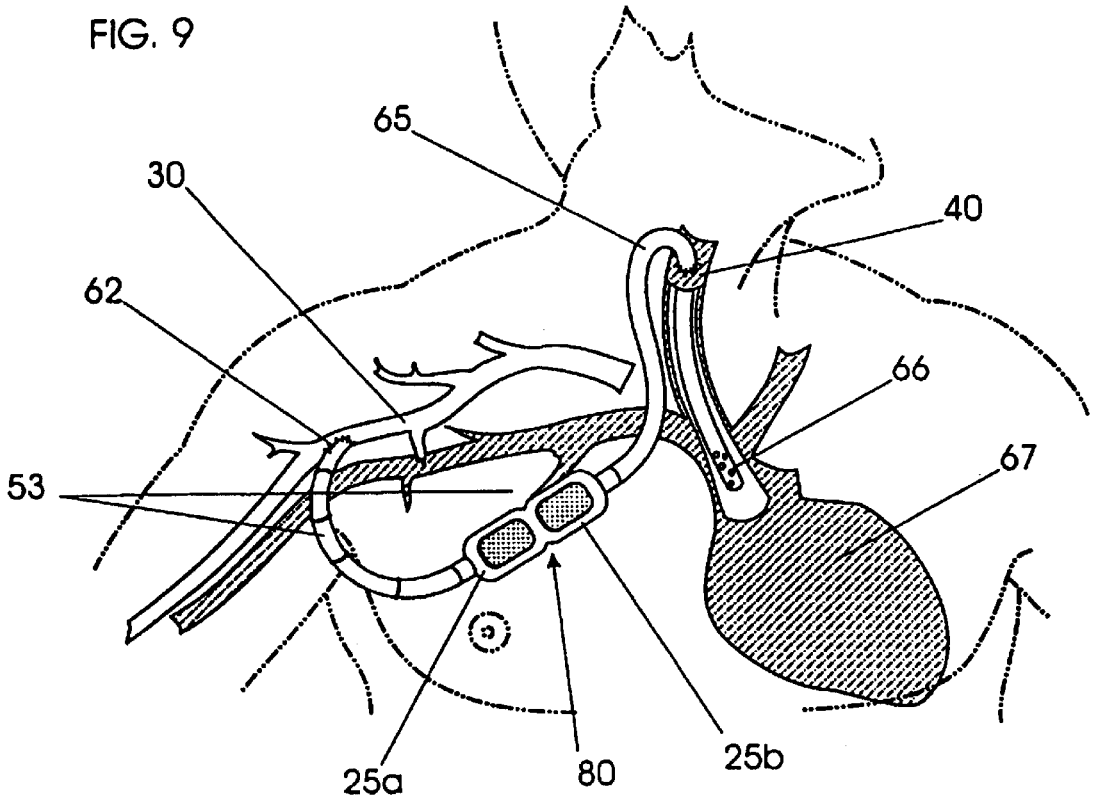
FIG. 9 depicts ringed PTFE tubing sewn to the subclavian artery and a dual access site coupled to the venous system at its other end.

FIG. 9 illustrates a dual needle access site 80 which is coupled via ringed PTFE 53 to the subclavian artery 30 and floated into the venous system 67 via silastic tubing 65. The dual site 80 provides additional access through 25a, 25b in approximately the same area with tubing (not shown) extending through the dual site 80.

Figure 10:
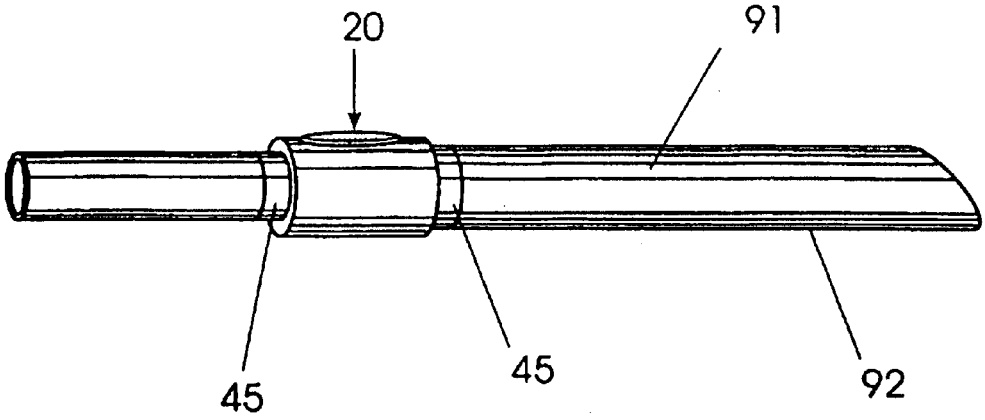
FIG. 10 shows a multi-layered variation at the venous end of the system.

FIG. 10 depicts a variation of the invention at the venous end wherein the outlet of the port 20 comprises PTFE tubing 91 located within a silastic catheter 92. The design is appropriate if thrombosis is a problem in the outlet silastic portion of the shunt.

FIG. 11 discloses a quick coupler 45 joining the PTFE [tubing] *outlet tube* 53 to the port 46 in the needle access site 20. A plastic or metal member 47 includes a portion 48 which engages the cylindrical tubing 10, an intermediate portion 49 extending perpendicularly outward and an end portion 43 tapered outwardly at an angle and including an inward projection 44. The projecting portion 44 of the member 47 engages a slot 54 in the port 46 firmly fixing the PTFE 10 therebetween. [45a] *Portion 48* is made of flexible material to allow a gentle curve in tubing as it exits/enters *the* port.

Figure 12:
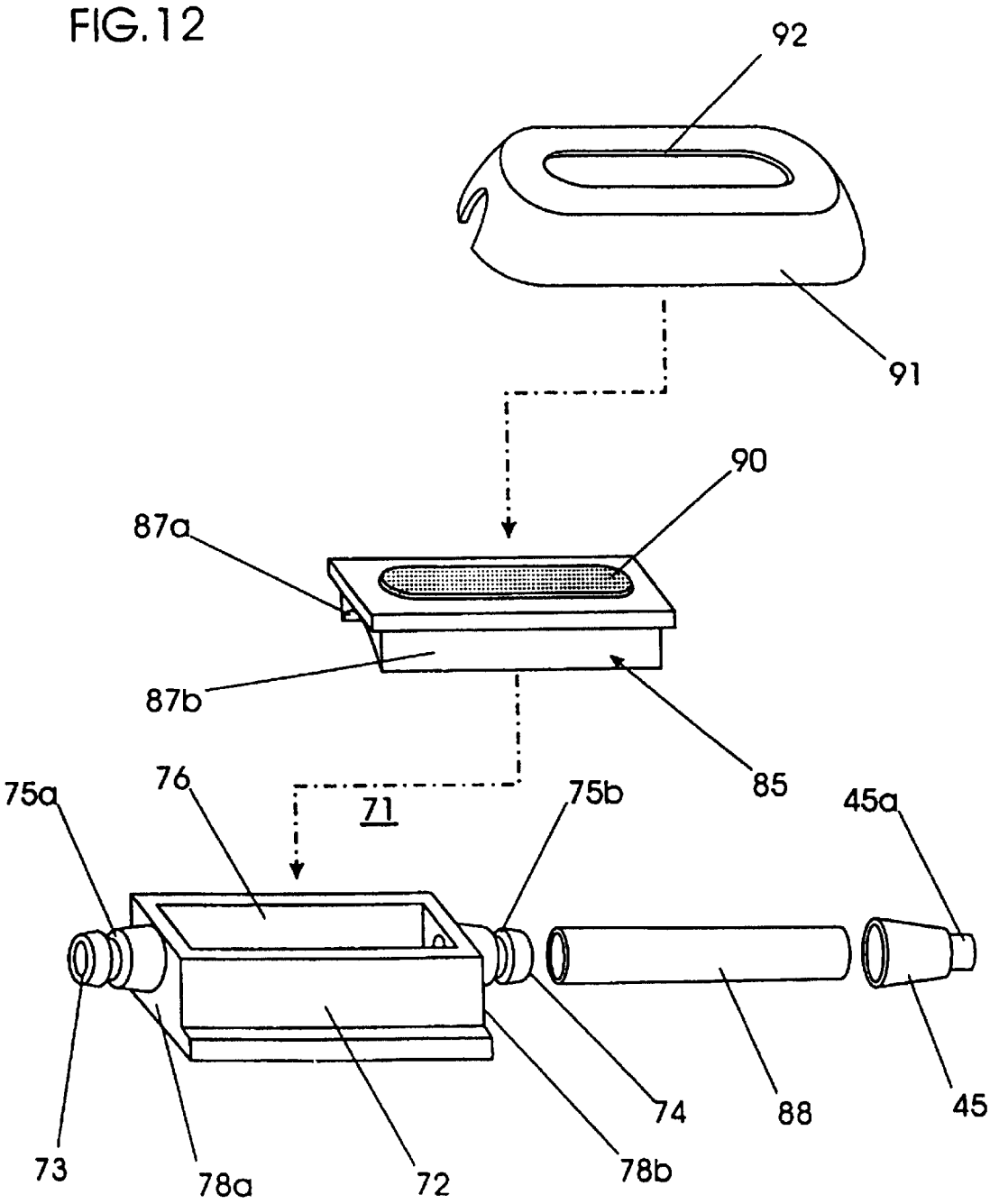
FIG. 12 is a unique port design utilized in conjunction with the system.

FIG. 12 is an exploded view of a new port embodiment wherein the port 71 comprises a frame 72 having an inlet 73 and an outlet 74. The plastic or metal frame 75 includes a recessed reservoir 76 and end walls 78a and 78b. An upper member 85 having a recess 86 and downwardly projecting sides 87a and 87b fits within walls 77a and 77b. The member 45 rapidly couples the PTFE tubing 10 to site 71 with tubing 88 which fits over the inlet coupling 73 and the outlet coupling 74 with recessed portions 75a and 75b which engage tubing 88a and 88b and have couplers 89a and 89b which slide over the tubing 88a, 88b to engage the couplings 73 and 74.

Figure 13:
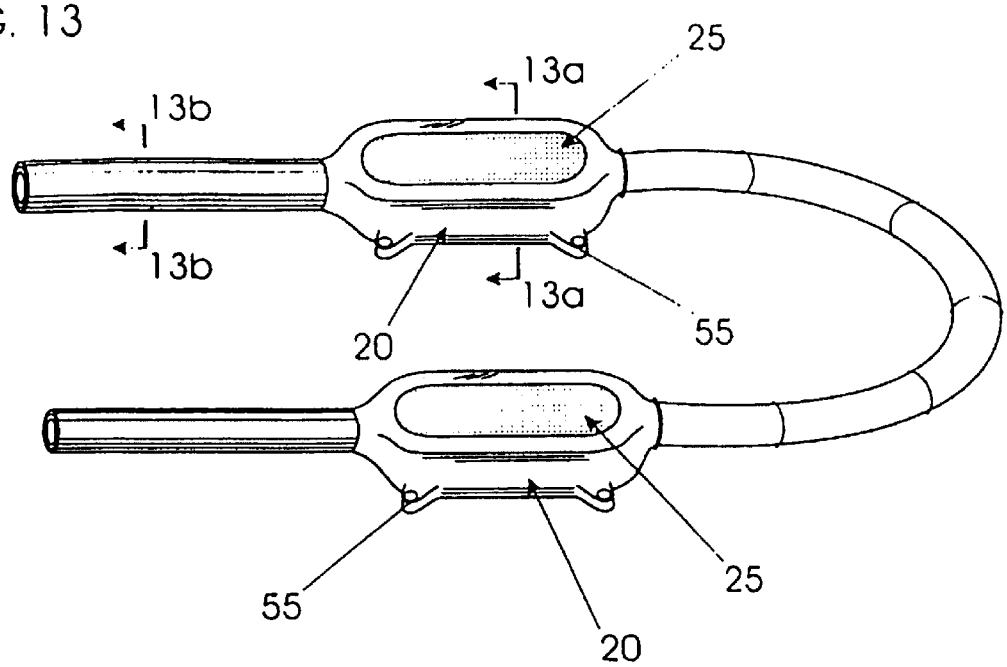
Figure 13A:
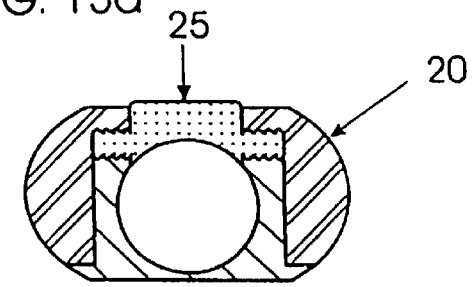
FIG. 13a and FIG. 13b show cross-sectional views which depict the internal construction of the invention with FIG. 13b illustrating multi-layered tubing; and, FIG. 14 shows a variation of the system entry through vein wall (i.e. not percutaneous or purse string) wherein a cuff, sewn to vein as indwelling portion, is floated down stream.
Figure 13B:
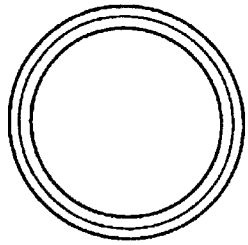

FIG. 13 shows a typical dual port system showing holes 55 where ports 20 can be fixed in place.

FIG. 14 discloses a cuff 56 which is made of PTFE and sewn to a vein. No physiological/functional venues anastomosis is created as blood is returned at the end of the system distant from the cuff. The silastic end 12 may still be lined with PTFE.

The upper member 86 includes an oval silicone access site 90 with an outer housing 91 which includes an aperture 92 surrounds the silicone oval 90. This embodiment provides a quick assembly for a needle access site 71.

The Squitieri Hemodialysis/Vascular Access System avoids creation of a venous anastomosis, a revolutionary advancement, i.e. there is no site for neointimal hyperplasia at a venous anastomosis which accounts for the vast majority of PTFE arteriovenous graft failures (60–80%). This is accomplished by returning the blood into a larger vein via an indwelling venous catheter 42. The site of blood return to the venous system is not fixed to the vein wall where neointimal hyperplasia occurs with the standard PTFE bridge graft. This feature represents a tremendous advantage over the present grafts.

As a further advantage, the system is not stagnant and prone to thrombosis, i.e. constant flow through the new system avoids the problem of clotting inherent in indwelling dual lumen venous catheters which remain stagnant when not in use. It also avoids need to flush catheters with heplock thereby reducing nursing costs to maintain the catheter.

The Squitieri system avoids externalization of components which are prone to infection. Since dual lumen catheters exit the skin 14, they frequently lead to sepsis requiring catheter removal despite subcutaneous tunneling. This new access is entirely subcutaneous.

Very importantly the system proposed herein, avoids problems with the aspiration of blood from the venous system and "positional" placement through continuous flow. A frequent problem with dual lumen catheters is their inability to draw blood from the venous system due to clot and fibrinous debris ball-valving at the tip of a catheter. This new system receives blood directly from arterial inflow which ensures high flow rates needed for shorter, more efficient dialysis runs. It also avoids the frequent problem of the catheter tip "sucking" on the vein wall inhibiting flow to the dialysis machine and rendering the access ineffective.

The system avoids recirculation seen with dual lumen catheters resulting in more efficient and more cost effective dialysis.

The system avoids the need for temporary access with incorporation of "Needle Access Sites" 20. A-V fistulas and gortex grafts must "mature" for several weeks before use. This creates a huge strain on the patient as well as the doctor to achieve temporary access while waiting to use the permanent access. Temporary access is very prone to infection, malfunction and vein destruction. By placing sites 20 designed to receive needles 15 along the new access, the system may be used the day it is inserted.

The system avoids PTFE needle site damage with the incorporation of "Needle Access Sites" 20. Needle access directly into PTFE is presently uncontrolled and user dependent. Often, PTFE is lacerated by access needles. While this system may be accessed via the PTFE segment, the needle receiving sites are the preferred method. This leads to excessive bleeding which requires excessive pressure to halt the bleeding causing thrombosis of the graft. "Needle Access Sites" 20 on the Squitieri access system allow safe, quick, and easy entry into the system and avoid the complications inherent in placing needles directly into PTFE. It also avoids perigraft bleeding which will compress and thrombose the graft. By elminating the long time needed to compress bleeding at the needle site, the system shortens dialysis runs.

The Squitieri system permits an easier, faster insertion technique. Only one anastomosis at the arterial end and a percutaneous placement of the venous end is required. A modification allows the system to be sutured to the vein wall while the system tubing is floated down stream from this site where the system enters the vein 40. This saves operating room time at thousands of dollars per hour. The technique is easier with faster replacement. It avoids difficult and time consuming revision of venous anastomosis required to repair venous outflow occluded by neointimal hyperplasia. If the system malfunctions, the silastic catheter end 65 slips out easily and the arterial PTFE end 53 is thrombectomized. New access sewn to the thrombectomized PTFE at the arterial end and the silastic venous end is replaced percutaneously via Seldinger technique or "open technique".

The end result of the above advantages translates into superior patency rates and a decreased complication rate with this new system. Patients are spared the repeated painful hospitalizations for failed access as well as the emotional trauma associated with this difficult condition. The physicians are spared the dilemma of how to best treat these patients. This system will have a large impact on the current practice of vascular access in areas such as hemodialysis; plasmapheresis; chemotherapy; hyperalimentation; and chronic blood draws.

While the invention has been explained by a detailed description of certain specific embodiments, it is understood that various modifications and substitutions can be made in any of them within the scope of the appended claims which are intended also to include equivalents of such embodiments.

What is claimed, is:

1. A Squitieri hemodialysis and vascular access system to shunt blood between a vein and an artery the system comprising:

(a) a first tube having a first end adapted to be connected to the artery and a second end;

(b) a second tube having a first end adapted to be connected to the vein and including a plurality of apertures extending therethrough and having a second end; and (c) a needle access port having a frame including a conduit extending therethrough, said frame having an inlet connected to the second end of the first tube and an outlet connected to the second end of the second tube to provide a flow path for blood and a silicone member protruding from the frame to provide access for needles into the flow path, wherein the needle access port includes:

an outer frame member having an upper surface including an aperture extending therethrough and downwardly extending walls about its periphery having inlet and outlet apertures, wherein the upper surface includes a lower portion having a plurality of teeth;

a silicone member mounted within the frame having a surface engaged by the frame teeth and an upwardly protruding portion extending through the frame aperture; and a second frame member having a transverse conduit extending between the inlet and outlet apertures, an upper surface having a plurality of teeth engaging the silicone member to effect a seal and wherein the second frame member is positioned within the walls of the first frame member.

2. The Squitieri hemodialysis and vascular access system of claim 1, wherein:

the first tube corresponds to PTFE tubing;

the second tube corresponds to silicone tubing; and the protruding silicone member has an oval configuration.

3. The Squitieri hemodialysis and vascular access system of claim 1, wherein the first tube includes rings mounted thereabout to provide additional strength.

4. The Squitieri hemodialysis and vascular access system of claim 1 further comprising:

a second needle access port having an inlet and an outlet and [silastic] *silicone* tubing coupling the inlet of the second needle access port to the outlet of the other needle access port and wherein the outlet of the second access port is coupled to the second end of the second tube.

5. The Squitieri hemodialysis and vascular access system of claim 1 wherein:

the first tube is provided as PTFE tubing which is adapted for attachment to the artery at one end and coupled to the access port at the other end; and the second tube is provided as silicone tubing which is coupled to the needle access port at one end and is capable of being floated within the vein at the other end.

6. The Squitieri hemodialysis and vascular access system of claim 1, wherein:

the first tube is inserted within an outer silicone tubing at the inlet to the needle access port.

7. The Squitieri hemodialysis and vascular access system of claim 1, further including:

an adjustable band mounted about the first tube at the inlet to the needle access port to regulate blood flow.

8. The Squitieri hemodialysis and vascular access system of claim 4, wherein:

a second needle access port is mounted to the needle access port, said ports having a single frame and a conduit extending longitudinally therethrough to the outlet tubing.

9. A Squitieri hemodialysis and vascular access system to shunt blood between a vein and an artery, the system including:

(a) a first tube having a first end adapted to be connected to the artery;

(b) a second tube having a first end adapted to be connected to the vein and including a plurality of apertures extending therethrough and having a second end;

(c) a needle access port having a frame including a conduit extending therethrough, said frame having an inlet connected to the second end of the first tube and an outlet connected to the second end of the second tube to provide a flow path for blood and a silicone member protruding from the frame to provide access for needles into the flow path; and a quick coupler for joining the first tube to the needle access port comprising a port member projecting outwardly from the frame inlet and having a circumferential slot extending thereabout, a cooperating member having an outer portion extending concentrically with the first tube and a portion extending outwardly therefrom and an outwardly sloped portion extending over the projecting port member and having an inner circumferential projection which engages the circumferential slot, and wherein the first tube extends over the port member to be engaged by the projecting portion of the cooperating member within the slot and a removable coupling which snaps over the cooperating member forcing it into a sealed engagement with the port member.

10. A Squitieri hemodialysis and vascular access system to shunt blood between a vein and an artery, the system including:

(a) a first tube having a first end adapted to be connected to the artery;

(b) a second tube having a first end adapted to be connected to the vein and including a plurality of apertures extending therethrough and having a second end; and (c) a needle access port having a frame including a conduit extending therethrough, said frame having an inlet connected to the second end of the first tube and an outlet connected to the second end of the second tube to provide a flow path for blood and a silicone member protruding from the frame to provide access for needles into the flow path, wherein the needle access port comprises:

a first member having a base, walls extending upwardly therefrom to form an enclosed area, and outwardly extending couplings on opposite walls thereof at the inlet and outlet of said port;

a second member having a top including an upper aperture, downwardly extending side walls engaging the walls of the first member and having a conduit extending from the inlet to the outlet and a silicone member projecting form the upper aperture to provide needle access; and a tube mounted over each coupling and a coupler which fits over each tube to seal the tubes to the couplings.

11. The Squitieri hemodialysis and vascular access system of claim 1, wherein:

the second tube is capable of being floated within a vein at the one end and the plurality of apertures in the second tube are distant from the site where the second tube is inserted into the vein, said second tube not being fixed to the vein wall.

[12. A hemodialysis and vascular access system comprising:

an arterialized indwelling venous catheter having a graft section provided from a material which is biocompatible with an artery, has a nonthrombogenic characteristic, which is adapted for long term attachment to an artery and which includes a region for repeated needle access and a catheter section, with a first end of said graft section adapted to be coupled to an artery and a portion of the catheter section adapted to be inserted within a vein at an insertion site, said catheter section portion having at least one opening in an end thereof with at least one of the at least one openings in the catheter section portion adapted to be within the vein itself and wherein the at least one opening is distant from the insertion site such that blood flows from the artery through the catheter and is returned to the vein through the at least one opening while providing laminar blood flow between the artery and the vein.]

[13. The hemodialysis and vascular access system of claim 12, further comprising:

at least one needle having a first end coupled to a hemodialysis device and having a second end adapted for insertion directly into said graft section of the catheter to shunt the blood flow through the dialysis device.]

[14. The hemodialysis and vascular access system of claim 13 wherein said graft section is provided from a first tube and said catheter section is provided from a second tube comprising multiple layers and a first end of said first tube is coupled to a first end of said second tube.]

[15. The hemodialysis and vascular access system of claim 14 wherein said first and second tubes are adapted for percutaneously placement.]

[16. The hemodialysis and vascular access system of claim 14 wherein the end of said second tube which is coupled to the first tube includes an enlarged portion in which the first end of said first tube is disposed.]

*17. A hemodialysis and vascular access system, comprising:*

*an arterialized indwelling venous catheter having a graft section provided from a material which is biocompatible with an artery, has a nonthrombogenic characteristic, which is adapted for long term attachment to an artery and which includes a region of repeated needle access and a catheter section, with a first end of said first graft section adapted to be coupled to an artery and a portion of the catheter section adapted to be inserted within a vein at an insertion site, said catheter section portion having an outside diameter which is less than an inner diameter of the vein and having at least one opening in an end thereof with at least one of the at least one openings in the catheter section portion adapted to be within the vein itself and wherein the at least one opening is distant from the insertion site such that, in operation, blood flows from the artery through the catheter and is returned to the vein through the at least one opening while providing laminar blood flow between the artery and the vein and blood also flows through the vein uninterrupted around at least an outer portion of said catheter; and*

*at least one needle having a first end coupled to a hemodialysis device and having a second end adapted for insertion directly into the arterialized indwelling venous catheter to shunt the blood flow through the dialysis device.*

*18. The hemodialysis and vascular access system of claim 17 wherein the graft section of said arterialized indwelling venous catheter is provided from a first tube and said catheter section is provided from a second tube comprising multiple layers and a first end of said first tube is coupled to a first end of said second tube.*

*19. The hemodialysis and vascular access system of claim 18 wherein said first and second tubes are adapted for percutaneous placement.*

*20. The hemodialysis and vascular access system of claim 18 wherein the end of said second tube which is coupled to the first tube includes an enlarged portion in which the first end of said first tube is disposed.*

*21. A hemodialysis and vascular access system as in claim 17, wherein the graft section comprises PTFE.*

*22. A hemodialysis and vascular access system as in claim 17, wherein the graft section comprises polyethylene terephthalate.*

*23. A hemodialysis and vascular access system as in claim 17, wherein the graft section has a diameter of approximately 7 mm.*

*24. A hemodialysis and vascular access system as in claim 17, wherein the first end of the graft section has a diameter of about 4 mm.*

*25. A hemodialysis and vascular access system as in claim 17, wherein the catheter section comprises silicone.*

*26. A hemodialysis and vascular access system as in claim 17, wherein a downstream end of the catheter section is provided with a bevel.*

*27. A hemodialysis and vascular access system as in claim 17, additionally comprising an access segment for receiving a needle to allow access to blood flowing through the catheter.*

*28. A hemodialysis and vascular access system as in claim 27, wherein the access segment comprises a self sealing material.*

*29. A hemodialysis and vascular access system as in claim 28, wherein the self sealing material comprises silicone.*

*30. A hemodialysis and vascular access system as in claim 28, wherein the access segment is removably connected to the access system.*

*31. A hemodialysis and vascular access system as in claim 27, further comprising a support structure in the access segment.*

*32. A hemodialysis and vascular access system as in claim 31, wherein the support structure comprises a frame.*

*33. A hemodialysis and vascular access system as in claim 31, wherein the support structure comprises ridges.*

*34. A hemodialysis and vascular access system as in claim 33, wherein the ridges comprise teeth.*

*35. A hemodialysis and vascular access system as in claim 17, wherein at least a portion of the indwelling venous catheter comprises multiple layers.*

*36. A hemodialysis and vascular access system as in claim 35, wherein the multiple layers comprise a first PTFE layer and a second silicone layer.*

*37. A hemodialysis and vascular access system as in claim 36, wherein the first PTFE layer is an inner PTFE layer and the second silicone layer is an outer silicone layer.*

*38. A hemodialysis and vascular access system as in claim 37, wherein the multiple layers further comprises a PTFE coating on the outer silicone layer.*

*39. A hemodialysis and vascular access system as in claim 17, wherein said graft section and said catheter section comprise a material selected from the group consisting of PTFE, silicone, or flexible plastic.*

*40. A hemodialysis and vascular access system as in claim 17, comprising first and second needle access sites.*

*41. A hemodialysis and vascular access system as in claim 17, wherein the catheter section comprises a long, flexible plastic tube.*

*42. A hemodialysis and vascular access system as in claim 17, wherein the region for repeated needle access comprises needle receiving sites(s) and comprises an internal chamber that is tubular in shape.*

*43. A hemodialysis and vascular access system as in claim 17, wherein the region for repeated needle access comprises a self-sealing material.*

*44. A hemodialysis and vascular access system as in claim 17, wherein the catheter section comprises a silicone section.*

*45. A hemodialysis and vascular access system as in claim 44, wherein the silicone section is lined with PTFE.*

*46. A hemodialysis and vascular access system as in claim 17, wherein the region of repeated needle access comprises multiple layers.*

*47. A hemodialysis and vascular access system as in claim 46, wherein the multiple layers comprise PTFE on the inside and silicone on the outside.*

*48. A hemodialysis and vascular access system as in claim 46, wherein the multiple layers comprise PTFE on the inside and silicone disposed outside of the PTFE.*

*49. A hemodialysis and vascular access system as in claim 17, wherein the material providing the graft section comprises a thrombus resistant coating.*

*50. A hemodialysis and vascular access system as in claim 49, wherein the thrombus resistant coating comprises heparin.*

*51. A hemodialysis and vascular access system as in claim 17, wherein a nonthrombenic characteristic is provided by continuous flow of blood through at least the graft section.*

* * * * *

UNITED STATES PATENT AND TRADEMARK OFFICE

CERTIFICATE OF CORRECTION

PATENT NO. : RE41,448 E
APPLICATION NO. : 10/219998
DATED : July 20, 2010
INVENTOR(S) : Rafael P. Squitieri It is certified that error appears in the above-identified patent and that said Letters Patent is hereby corrected as shown below:

Title page 2, in Item (56), Column 2, line 23, under Other Publications change "Techinique" to --Technique--.

In Column 1, line 33, change ""aneursymbol" to --aneursymol--.

In Column 2, line 12, after "inventions" insert --.--.

In Column 2, line 57, change "fistulu" to --fistula--.

In Column 4, line 50, change "exchangability" to --exchangeability--.

In Column 5, line 25, change "thrombosis and" to --thrombosis rate and--.

In Column 6, line 7, change "The" to --This--.

In Column 7, line 35, change "elminating" to --eliminating--.

In Column 12, line 51, in Claim 51, change "nonthrombenic" to --nonthrombogenic--.

Signed and Sealed this
Twenty-second Day of February, 2011

David J. Kappos

David J. Kappos
*Director of the United States Patent and Trademark Office*

UNITED STATES PATENT AND TRADEMARK OFFICE

CERTIFICATE OF CORRECTION

PATENT NO. : RE41,448 E
APPLICATION NO. : 10/219998
DATED : July 20, 2010
INVENTOR(S) : Rafael P. Squitieri It is certified that error appears in the above-identified patent and that said Letters Patent is hereby corrected as shown below:

At Column 1, Line 12 through 16, Change "Notice: More than one reissue application has been filed for the reissue of U.S. Pat. No. 6,102,884. The reissue applications are U.S. application Ser. No. 10/219,998 (the present application) and U.S. application Ser. No. 11/417,658, which is a continuation reissue of U.S. Pat. No. 6,102,884." to --Notice: More than one reissue application has been filed for the reissue of U.S. Pat. No. 6,102,884. The reissue applications are U.S. application Ser. No. 10/219,998 (the present application) and U.S. application Ser. Nos. 11/417,658 and 12/688,716 which are continuation reissues of U.S. Pat. No. 6,102,884.--

Signed and Sealed this
Fifteenth Day of May, 2012

David J. Kappos

David J. Kappos
*Director of the United States Patent and Trademark Office*